(12) United States Patent
Fadel et al.

(10) Patent No.: US 11,986,578 B2
(45) Date of Patent: May 21, 2024

(54) MALODOUR COUNTERACTING AND FRAGRANCE DELIVERY SYSTEM

(71) Applicant: Firmenich SA, Geneva (CH)

(72) Inventors: Addi Fadel, Plainsboro, NJ (US); Nicholas O'Leary, Plainsboro, NJ (US)

(73) Assignee: FIRMENICH SA, Satigny (CH)

( * ) Notice: Subject to any disclaimer, the term of this patent is extended or adjusted under 35 U.S.C. 154(b) by 734 days.

(21) Appl. No.: 16/617,092

(22) PCT Filed: May 30, 2018

(86) PCT No.: PCT/EP2018/064267
§ 371 (c)(1),
(2) Date: Nov. 26, 2019

(87) PCT Pub. No.: WO2018/220059
PCT Pub. Date: Dec. 6, 2018

(65) Prior Publication Data
US 2020/0164098 A1    May 28, 2020

Related U.S. Application Data (60) Provisional application No. 62/512,416, filed on May 30, 2017.

(30) Foreign Application Priority Data

Oct. 24, 2017    (EP) .................................. 17198076

(51) Int. Cl.
*A61L 9/12*    (2006.01)
*A61L 9/014*    (2006.01)
*A61L 9/04*    (2006.01)
*B01D 53/04*    (2006.01)
*A01M 1/20*    (2006.01)

(52) U.S. Cl.
CPC ................. *A61L 9/12* (2013.01); *A61L 9/014* (2013.01); *A61L 9/042* (2013.01); *A61L 9/046* (2013.01); *B01D 53/04* (2013.01); *A01M 1/20* (2013.01); *A61L 2209/22* (2013.01); *B01D 2253/3425* (2013.01); *B01D 2257/90* (2013.01)

(58) Field of Classification Search
None
See application file for complete search history.

(56) References Cited

U.S. PATENT DOCUMENTS

| | | | |
|---|---|---|---|
| 9,457,117 B2 | 10/2016 | O'Leary et al. | |
| 2005/0001031 A1 | 1/2005 | Akiho et al. | |
| 2005/0265904 A1 | 12/2005 | Hardy et al. | |

(Continued)

FOREIGN PATENT DOCUMENTS

| | | |
|---|---|---|
| CN | 1897809 A | 1/2007 |
| CN | 101347630 A | 1/2009 |

(Continued)

OTHER PUBLICATIONS

Aibe, N. JP2005288380A—translated document (Year: 2005).*

(Continued)

*Primary Examiner* — Jelitza M Perez (57) ABSTRACT

Described herein is a device, and consumer articles associated therewith, for dispensing an active composition and absorbing malodors in the surrounding space.

18 Claims, 4 Drawing Sheets

(56) References Cited

U.S. PATENT DOCUMENTS

2007/0183940 A1* 8/2007 Yamamoto .............. A61L 9/042
 422/124
2014/0076984 A1 3/2014 Irwin et al.

FOREIGN PATENT DOCUMENTS

| EP | 1698288 A1 | 6/2006 |
| JP | H7-236399 A | 9/1995 |
| JP | H11-155942 A | 6/1999 |
| JP | 2005288380 A * | 10/2005 |
| JP | 2005288380 A | 10/2005 |

OTHER PUBLICATIONS

International Search Report and Written Opinion for International Application No. PCT/EP2018/064267, dated Sep. 19, 2018. 16 pages.
Calandra et al., "An HPLC method for hydroperoxides derived from limonene and linalool in citrus oils, using post-column luminol-mediated chemiluminescence detection", Flavor and Fragrance Journal, Published 2015, pp. 121-130, vol. 30.

* cited by examiner

MALODOUR COUNTERACTING AND FRAGRANCE DELIVERY SYSTEM

CROSS REFERENCE TO RELATED APPLICATIONS

The present application is a U.S. National Phase Application of PCT/EP2018/064267, filed on May 30, 2018, which claims the benefit of priority to U.S. Provisional Patent Application Ser. No. 62/512,416, filed on May 30, 2017, and European Patent Application Serial No. 17198076.6, filed on Oct. 24, 2017, the entire contents of which are hereby incorporated by reference herein.

FIELD OF THE INVENTION

The present disclosure relates to the field of perfumery and more precisely it concerns a device, and the consumer articles associated therewith, for dispensing an active composition and absorbing malodors in the surrounding space.

BACKGROUND

Devices for dispensing an active liquid in the surrounding space are known. For example, one type device is the so-called wick-based device, which comprises a reservoir, a wick and an emanating body from which the active liquid evaporates. One problem of such wick-based devices is the difficulty to achieve a controlled release in the surroundings of the active liquid in order to avoid that the evaporation of the active liquid is too quick or too slow. Other problems associated with of wick-based devices include their complexity and requirement for large volumes of active compositions in order to distribute active compositions efficiently.

Consequently, a need exists for simple and efficient delivery device for active compositions that does not require large volumes of active compositions.

SUMMARY

One aspect provides a device comprising:
a) a body portion,
wherein the body portion comprises a honeycomb comprised of a porous material,
wherein the honeycomb comprises a plurality of individual cells bounded with one another,
wherein the plurality of cells are bounded at a density,
wherein each cell within the plurality comprises a hollow tube, having a wall, a first end, and a second end,
wherein the wall has an inner surface defining an inner dimension of the hollow tube,
wherein the wall has a thickness,
wherein the first and second ends of the tube are open,
wherein the first end of each individual cell within the plurality are aligned,
wherein the second end of each individual cell within the plurality are aligned,
wherein the distance between the first end and the second end of each individual cell within the plurality, and the inner dimension of the hollow tube of each individual cell within the plurality define a volume of each individual cell within the plurality,
wherein the distance between the first end and the second end of each individual cell within the plurality, the inner surface and inner dimension of the hollow tube of each individual cell within the plurality define a surface area within each individual cell within the plurality,
wherein the sum of each surface area within each individual cell within the plurality defines a total surface area of the plurality of cells, wherein a first end of the plurality of cells define a bottom surface of the body portion,
wherein a second end of the plurality of cells define a top surface of the body portion,
wherein the body portion has at least one side surface,
wherein the at least one side surface is continuous planar surface; and
b) an active composition,
wherein each individual cell within the plurality is configured to draw in the active composition into the volume,
wherein the porous material of the body portion is configured to absorb the active composition, and
wherein the porous material of the body portion is configured to disperse the active composition via evaporation.

In one aspect, the porous material is selected from the group consisting of: charcoal, ceramic, plastic, clay, cellulose, and mixtures thereof.

In one aspect, the body portion has a cross-sectional shape selected from the group consisting of: an irregular shape, a square, a rectangle, a circle, an ellipse, a rhombus, a semi-circle, and a trapezium.

In one aspect, the individual cells within the plurality have a cross-sectional shape selected from the group consisting of: an irregular shape, a square, a rectangle, a circle, an ellipse, a rhombus, a semi-circle, and a trapezium.

In one aspect, the individual cells within the plurality are co-aligned.

In one aspect, the individual cells within the plurality are straight.

In one aspect, the density is from 50 to 1000 cells per square inch.

In one aspect, the total surface area of the plurality of cells is from $1000$ $cm^2$ to $3000$ $cm^2$.

In one aspect, the porous material of the body portion is configured to disperse the active composition via evaporation for a period of time up to one month.

In one aspect, the device further comprises a reservoir, configured to fluidly connect with the bottom surface of the device, wherein fluid connection is configured to draw the active composition into the volume of each individual cell within the plurality.

In one aspect, the dispensing of the active composition via evaporation is increased by increasing airflow through the plurality of cells from the first end and the second end of the plurality of cells.

In one aspect, the porous material of the body portion is configured to absorb molecules having malodors.

In one aspect, the absorption of molecules having malodors is increased by increasing airflow through the plurality of cells from the first end and the second end of the plurality of cells.

One aspect provides a method of dispensing an active composition into a surrounding space, comprising providing a device according to some aspects presented herein, placing the device into a space, and allowing the active composition to evaporate from the device.

One aspect provides a kit, comprising a device according to some aspects presented herein and at least one active composition.

DETAILED DESCRIPTION

In the following description, reference is made to specific embodiments which may be practiced, which is shown by way of illustration. These embodiments are described in detail to enable those skilled in the art to practice the disclosure described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

The present disclosure relates to the field of perfumery and more precisely it concerns a device, and the consumer articles associated therewith, for dispensing an active composition and absorbing malodors in the surrounding space. In some aspects, the body portion of the device has a high surface area and is made of a material that is capable of absorbing and evaporating active compositions. The body portion of the device may have any cross-sectional shape, such as, for example, an irregular shape, a square shape, a rectangular shape, a circular shape, an elliptical shape, a rhomboid shape, a semi-circular shape, a trapezoidal shape and the like. In some aspects, the body portion of the device comprises a plurality of cells bounded with one another, where the plurality of cells is configured to draw the active composition into the body portion of the device. Furthermore, the plurality of cells bounded with one another is configured to allow air to flow through the body portion from the bottom surface of the device to the top surface (10) of the device, or vice versa.

Examples of devices according some aspects provided herein are shown in FIGS. 1 to 4.

Figure 1:
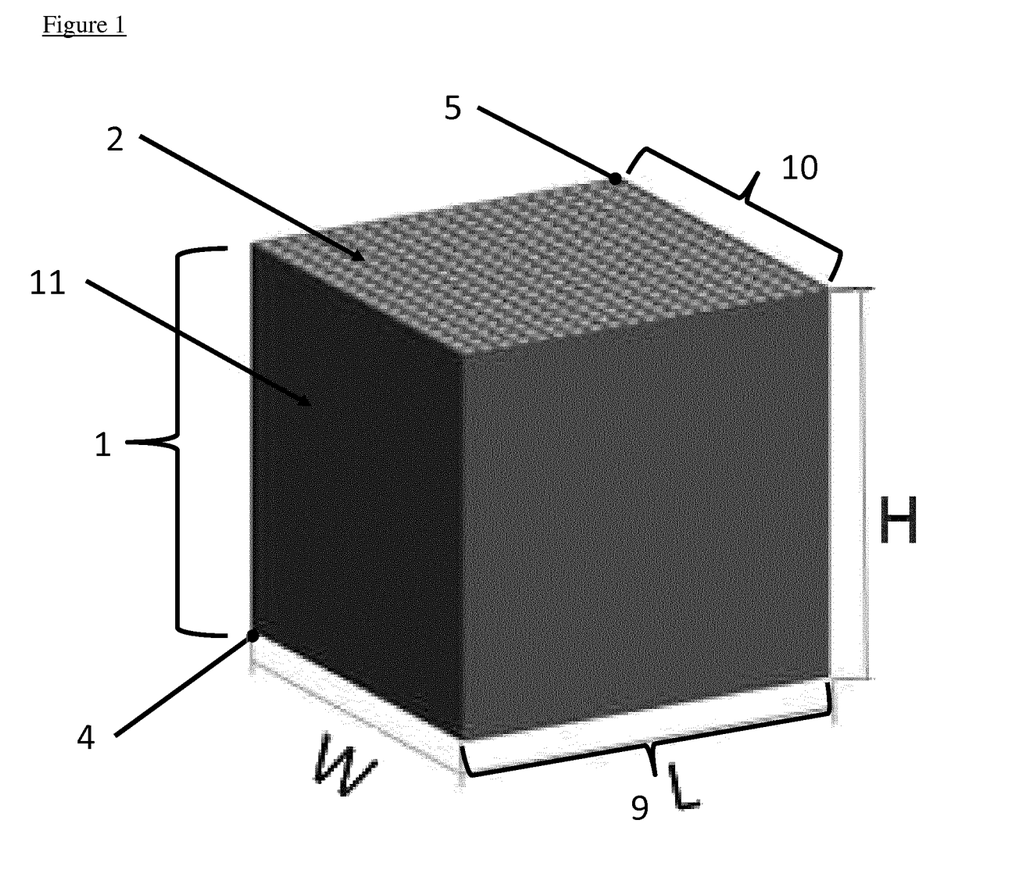
FIG. 1 shows a device according to certain aspects presented herein.
Figure 2:
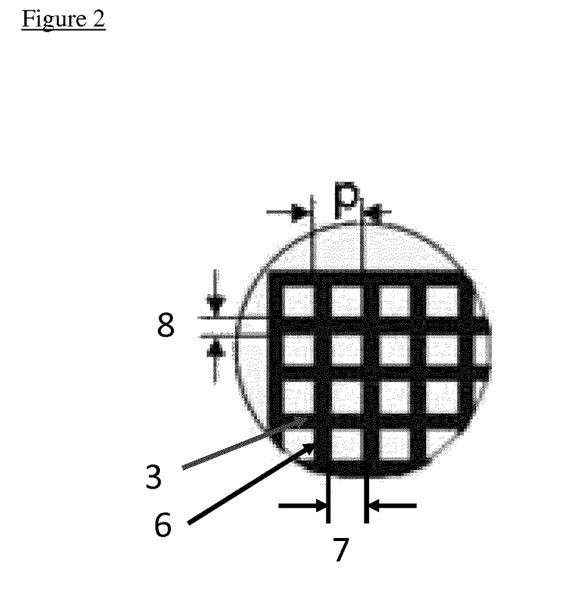
FIG. 2 shows a close-up view of the individual cells of a device according to certain aspects presented herein.
Figure 3:
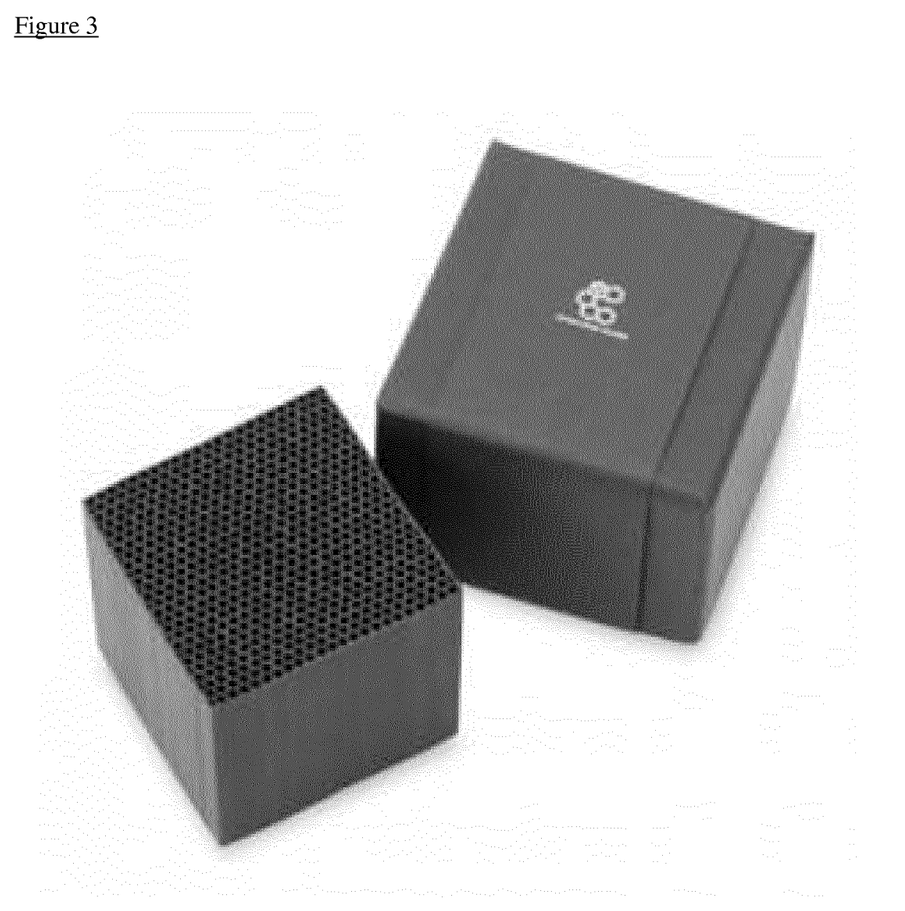
FIG. 3 shows another device according to certain aspects presented herein.
Figure 4:
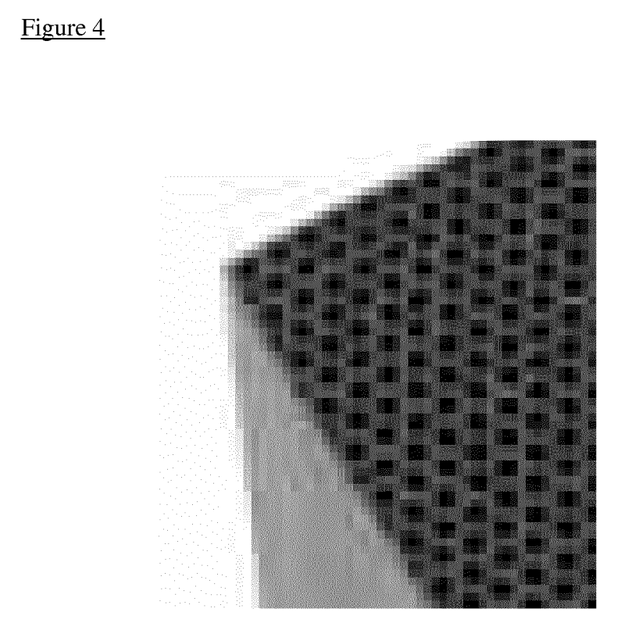
FIG. 4 shows a close-up view of the individual cells of the other device according to certain aspects presented herein.

The Device: Referring to FIGS. 1 and 2, some aspects presented herein provide a device comprising:

a) a body portion (1),
wherein the body portion (1) comprises a honeycomb comprised of a porous material,
wherein the honeycomb comprises a plurality of individual cells (2) bounded with one another,
wherein the plurality of individual cells (2) have a spacing (p) between each other,
wherein the plurality of cells (2) are bounded at a density,
wherein each cell (2) within the plurality comprises a hollow tube, having a wall (3), a first end (4), and a second end (5),
wherein the wall (3) has an inner surface (6) defining an inner dimension (7) of the hollow tube,
wherein the wall (3) has a thickness (8),
wherein the first (4) and second (5) ends of the tube are open,
wherein the first end (4) of each individual cell (2) within the plurality are aligned,
wherein the second end (5) of each individual cell (2) within the plurality are aligned,
wherein the distance between the first end (4) and the second end (4) of each individual cell (2) within the plurality, and the inner dimension (7) of the hollow tube of each individual cell (2) within the plurality define a volume of each individual cell (2) within the plurality,
wherein the distance between the first end (4) and the second end (5) of each individual cell (2) within the plurality, the inner surface (6) and inner dimension (7) of the hollow tube of each individual cell (2) within the plurality define a surface area within each individual cell (2) within the plurality,
wherein the sum of each surface area within each individual cell within the plurality defines a total surface area of the plurality of cells,
wherein a first end of the plurality of cells define a bottom surface (9) of the body portion (1),
wherein a second end of the plurality of cells define a top surface (10) of the body portion (1),
wherein the body portion has at least one side surface (11),
wherein the at least one side surface (11) is continuous planar surface; and b) an active composition,
wherein each individual cell (2) within the plurality is configured to draw in the active composition into the volume,
wherein the porous material of the body portion (1) is configured to absorb the active composition, and
wherein the porous material of the body portion (1) is configured to disperse the active composition via evaporation.

As used herein, the term "honeycomb" refers to an arrangement of individual cells to form a plurality of individual cells in an array. The plurality may comprise more than one individual cell. Non-limiting examples of arrays of individual cells include a 10×10 array, an 18×18 array, a 30×30 array, and the like.

As used herein, the term "continuous planar surface" refers to a surface having no holes or perforations that extend through the entire thickness of the surface.

The body portion (1) can be made of any one or more of a variety of porous materials. Suitable porous materials for the body portion (1) include, but are not limited to: porous porcelain materials, plastics, molded ceramics, glass fibers, clay, activated carbon, cellulose, and the like.

In some aspects, the porous material is selected from the group consisting of: charcoal, ceramic, plastic, clay, cellulose, and mixtures thereof. In some aspects, the porous material is charcoal. In some embodiments, the charcoal is activated charcoal.

The body portion (1) may be formed by any suitable method, readily selected by one of ordinary skill in the art. Non-limiting examples of methods to form the body portion (1) include casting, extrusion, 3-D printing, and the like.

Without intending to be limited to any particular theory, the porous material is configured to absorb the active composition, wherein the active composition infiltrates and becomes situated into the pores of the porous material, such that no, or a merely negligible amount of the active composition remains within the volume of each individual cell (2) within the plurality. Additionally, the porous material is configured to allow the active composition to evaporate from the pores of the porous material at a relatively steady rate during the life of the device, wherein the evaporation of the active composition disperses the active composition into the surrounding space.

In some aspects, the pore size of the porous material is from 5 µm to 200 µm.

In some aspects, the body portion (1) can absorb from 0.01 g to 0.1 g of the active composition per square centimeter of the total surface area of the plurality of individual cells. Alternatively, the body portion (1) can absorb from 0.02 g to 0.08 g of the active composition per square centimeter of the total surface area of the plurality of individual cells.

In one alternative aspect, the porous material is configured to absorb the active composition, wherein the active composition infiltrates and becomes situated into the pores of the porous material and within the hollow tube of each individual cell (2) within the plurality of cells. In some aspects, the active composition may occupy all, or a portion of the hollow tube of each individual cell (2) within the plurality of cells.

In some aspects, the life of the device is one month or greater. Accordingly, in some aspects, the porous material of the body portion is configured to disperse the active composition via evaporation for a period of time up to one month.

In some aspects, the porous material is configured to ensure that the amount of active composition that evaporates from the body portion (1) is in an amount sufficient to ensure the active composition is at, or above its odor threshold in the surrounding space.

Furthermore, in some aspects, the porous material is configured to ensure the amount of active composition that is released from the device into the surrounding space remains relatively constant throughout the lifetime of the device. In some aspects, maintaining a relatively constant throughout the lifetime of the product is achieved by ensuring the rate of evaporation from the porous material is the same as the rate at which a user becomes habituated to the perfume, and/or the rate at which the levels of the active composition in the surrounding space fall below its odor threshold.

Referring to FIG. 2, wherein several individual cells are shown in greater detail, it can be seen that each individual cell 2) within the plurality comprises a hollow tube, having a wall (3), a first end (4), and a second end (5). Each individual cell (2) comprises a tube wherein the wall (3) has an inner surface (6) defining an inner dimension (7) of the hollow tube, wherein the wall (3) has a thickness (8), and the first (4) and second (5) ends of the tube are open.

In some aspects, the distance between the first end (4) and the second end (4) of each individual cell (2) within the plurality, and the inner dimension (7) of the hollow tube of each individual cell (2) within the plurality define a volume of each individual cell (2) within the plurality. The distance between the first end (4) and the second end (5) of each individual cell (2) within the plurality, the inner surface (6) and inner dimension (7) of the hollow tube of each individual cell (2) within the plurality define a surface area within each individual cell (2) within the plurality, wherein the sum of each surface area within each individual cell within the plurality defines a total surface area of the plurality of cells.

It can be readily appreciated that the total surface area of the plurality of cells is greater than the surface area surface area of the at least one side surface (11). In some aspects, the total surface area of the plurality of cells is influenced by a number of factors, including, but not limited to, the dimensions of the device, the thickness of the wall (3) of the individual cell, the inner dimension (7) of the hollow tube, the density of the array of the individual cells, and the like.

Referring Example 1 below, and FIG. 1 by way of a non-limiting example of a device having a regular shape, in some aspects, the total surface area of the plurality of cells is the surface area of each cell multiplied by the total number of cells. The device described in Example 1 is a cube, where each side of the cube is 46 mm, and a bulk volume of approximately 100 cm$^3$. The density of the plurality of cells is 100 cells per square inch, the thickness of the wall (3) of the individual cells is 0.50 mm, and the spacing (p) of each individual cell is 2.54 mm. Accordingly, the body portion (1) comprises 324 cells, in an 18×18 array. The surface area of each cell is 375 mm$^2$. Accordingly, the total surface area of the plurality of cells is 121500 mm$^2$ (1215 cm$^2$ or 188 sq·in. or 1.3 sq·ft).

Referring Example 2 below, the device described is cuboidal, having a width and length of 43 mm, and a height of 42 mm. The cells are hexagonal, the density of the plurality of cells is 200 cells per square inch. The thickness of the wall (3) of the individual cells is 0.37 mm. The cells are arranged in an array of 585 cells. The surface area of each cell is 213 mm$^2$. Accordingly, the total surface area of the plurality of cells is 124989 mm$^2$ (1250 cm$^2$ or 194 sq·in. or 1.34 sq·ft).

Referring Example 3 below, the device described is a cube, where each side of the cube is 46 mm, and a bulk volume of approximately 100 cm$^3$. The density of the plurality of cells is 300 cells per square inch, the thickness of the wall (3) of the individual cells is 0.30 mm, and the spacing (p) of each individual cell is 1.47 mm. Accordingly, the body portion (1) comprises 961 cells, in a 31×31 array. The surface area of each cell is 215 mm$^2$. Accordingly, the total surface area of the plurality of cells is 206616 mm$^2$ (2066 cm$^2$ or 320 sq·in. or 2.2 sq·ft).

Accordingly, the density of the individual cells can alter the total surface area:volume ratio of the device. One of ordinary skill in the art can readily appreciate that the surface area:volume ratio of the device may be configured to ensure the amount of active composition that is absorbed by the body portion (1) is in an amount sufficient to ensure the amount of active composition that is released from the device into the surrounding space remains relatively constant throughout the lifetime of the device, and/or is in an amount sufficient to be above its odor threshold in the surrounding space.

In some aspects, the total surface area of the plurality of individual cells is configured to ensure the amount of active composition that is absorbed by the body portion (1) is in an amount sufficient to ensure the amount of active composition that is released from the device into the surrounding space remains relatively constant throughout the lifetime of the device, and/or is in an amount sufficient to be above its odor threshold in the surrounding space.

In some aspects, the individual cells (2) within the plurality have a cross-sectional shape selected from the group consisting of: an irregular shape, a square, a rectangle, a circle, an ellipse, a rhombus, a semi-circle, and a trapezium.

In one aspect, the dispensing of the active composition via evaporation is increased by increasing airflow through the plurality of individual cells (2) from the first end and the second end of the plurality of individual cells (2).

As used herein, the term "rate" refers to the amount of active composition, per unit of time, which is emitted into the surroundings during a given frame of time, or alternatively, a weight loss of active composition from the device per a given period of time.

As used herein, the term "essentially constant rate" refers to a rate which can oscillate in a range comprised between approximately 80% and approximately 120% of the mean rate, alternatively between 90% and 110%, during a period of at least 20 days, or even 25 days, of use of the device according to some aspects presented herein.

Without intending to be limited to any particular theory, the increased airflow increases the rate at which the active composition evaporates from the porous material, thus increasing the rate of dispersion of the active composition into the surrounding space. In some aspects, the increase in the rate of dispersion is 10%, or 20%, or 30%, or 40%, or 50%, or 60%, or 70%, or 80%, or 90%, or 100%, or 150%, or 200%, or 250%, or 300%, or 350%, or 400%, or 450%, or 500%, or greater.

In some aspects, an increased rate of dispersion of the active composition results in a greater amount of the active composition in the surrounding space.

In some aspects, the airflow through the plurality of individual cells (2) from the first end and the second end of the plurality of individual cells (2) is increased via a fan, or other suitable air moving device. Non-limiting examples of suitable air moving devices are disclosed in U.S. Pat. No. 9,457,117, and U.S. Patent Application Publication No. 2005/01031 A1.

In some aspects, the porous material of the body portion (1) is configured to absorb molecules having malodors. Smells perceived as malodorous exist in many environments and are experienced in our daily life. The odorants eliciting this negative association can for example consist of commercial and residential environment malodors which can be generated by waste products, trash receptacles, toilets, cat litter, and food handling and processing. Toilet (in particular feces), kitchen and body malodor, are just a few of the common environmental sources of malodors in daily life. Malodors are usually complex mixtures of more than one malodorant compound which may typically include various amines, thiols, sulfides, short chain aliphatic and unsaturated acids, e.g. fatty acids, and their derivatives. Residential or body related malodors are typically due to various chemical compounds such as indole, skatole, and methanethiol found in feces malodor; piperidine and morpholine found in urine; pyridine and triethyl amine found in kitchen and garbage malodors; and short chain fatty acids, such as 3-methyl-3-hydroxyhexanoic acid, 3-methylhexanoic acid or 3-20 methyl-2-hexenoic acid, found in axillary malodors.

Without intending to be limited to any particular theory, the porous material of the body portion (1) is capable of absorbing malodor compounds present in the surrounding space, thereby lowering the concentration of the malodor compounds below their respective odor threshold, thus neutralizing the malodors.

In some aspects, the absorption of molecules having malodors is increased by increasing airflow through the plurality of individual cells (2) from the first end and the second end of the plurality of individual cells (2). In some aspects, air from the surrounding space containing malodor compounds is drawn into the body portion (1) through the bottom surface (9) of the body portion. In some aspects, malodor compounds are absorbed as the air passes through the body portion (1), and the air exiting the top surface (10) of the body portion comprises an active composition and a lower concentration of malodor compounds.

Without intending to be limited to any particular theory, the increased airflow increases the rate at which the malodor compounds are absorbed by the porous material. In some aspects, the increase in the rate of absorption is 10%, or 20%, or 30%, or 40%, or 50%, or 60%, or 70%, or 80%, or 90%, or 100%, or 150%, or 200%, or 250%, or 300%, or 350%, or 400%, or 450%, or 500%, or greater.

In some aspects, an increased rate of absorption of the malodor compounds results in a lower amount of the malodor compounds in the surrounding space.

In some aspects, the device further comprises a reservoir, configured to fluidly connect with the bottom surface (9) of the device, wherein fluid connection is configured to draw the active composition into the volume of each individual cell (2) within the plurality.

In some aspects, the fluid connection is direct, wherein the reservoir is connected directly to the bottom surface (9) of the device. In alternate aspects, the fluid connection is in-direct, in that the reservoir is separate to the bottom surface (9) of the device, and the contents of the reservoir are transferred to the bottom surface (9) of the device by means of a tube, wick, conduit, or any other suitable means of conveying a liquid. Non-limiting examples of reservoirs and fluid connections are disclosed in U.S. Pat. No. 9,457,117, and U.S. Patent Application Publication No. 2005/01031 A1.

In some aspects, the device is reusable once the active composition is depleted. In some aspects, in order to replenish a supply of the active composition, a user may immerse the body portion (1) into a solution of the active composition, thereby allowing the active composition to be drawn into each individual (2) within the plurality and be absorbed by the porous material of the body portion (1). Alternatively, the supply of the active composition may be replenished by refilling the reservoir.

It can be readily appreciated that a user may select a particular active composition to introduce into the body portion, and introduce the selected active composition, either by immersion of the body portion (1) into the selected active composition, or by filling the reservoir with the selected active composition.

In some aspects, where the device is refillable, a user may employ a volatile liquid composition that evaporates substantially during the desired use period of the device. By evaporates substantially, it is meant the mass of the volatile liquid evaporated during the use period is greater than 75% of the initial mass of the volatile liquid absorbed into the device. Alternatively, in some aspects, the mass of the volatile liquid evaporated during the use period is greater than 80% of the initial mass of the volatile liquid absorbed into the device. Alternatively, in some aspects, the mass of the volatile liquid evaporated during the use period is greater than 85% of the initial mass of the volatile liquid absorbed into the device. In some aspects, the liquid composition comprises less than 20% by weight ingredients with a vapor pressure of less than 0.01 mmHg at 20° C.

In some aspects, the dispersion of the active composition may be prevented, or blocked. Methods to prevent or block the dispersion of the active composition include, but are not limited to sealing the top and bottom surfaces of the body portion (1), preventing airflow through the body portion, and the like.

The Active Composition: As used herein, the term "active composition" refers to a liquid which is at least partially volatile, i.e., can evaporate, and which is able to impart a fragrance or other benefit to the surrounding space.

The active composition may contain between 40% by weight and 100% by weight fragrance-chemicals or essential oils; alternatively between 60% by weight and 100% by weight fragrance-chemicals or essential oils. The balance of these formulations can include solvents, dyes, colorants, anti-oxidants, UV inhibitors, bittering agents, etc. as are generally known to skilled artisans. Any particular formulations can be tested for determining the optimum total surface area of the plurality of honeycomb structures for dispensing the active formulation.

In some aspects, the active composition is a perfume. As perfume there can be used any ingredient or mixture of ingredients currently used in perfumery, i.e. capable of exercising a perfuming action. More often, however, a perfume will be a more or less complex mixture of ingredients of natural or synthetic origin. The nature and type of the ingredients do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitrites, terpene hydrocarbons, nitrogenous or *sulphurous* heterocyclic compounds and essential oils of natural or synthetic origin. Many of these ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery.

In some aspects, the perfuming action may further comprise providing a sensorial and/or emotional benefit, or, alternatively, the perfuming action may be configured to prevent the habituation of the user to the perfume. In some aspects, the sensorial and/or emotional benefit may be provided by the addition of an additional agent to the active composition. For example, by way of illustration, the active composition may further comprise a cooling compound, that imparts a cooling sensation to a user.

In some aspects, the active composition is configured to uniformly evaporate over the lifetime of the device. In some aspects, the term "uniformly evaporate" refers to the rate of evaporation. However, in some aspects, the term "uniformly evaporate" refers to the performance, such as, the perceived intensity of scent in the surrounding space, wherein the performance of the device remains at a certain level throughout the lifetime of the device.

In some aspects, the active composition is configured to uniformly evaporate, leaving 10% or less of the active composition in the device after one month. In some aspects, the active composition comprises ingredients having vapor pressures sufficient to ensure the active composition uniformly evaporates, leaving 10% or less of the active composition in the device after one month.

In some aspects, the active composition comprises ingredients having vapor pressures sufficient to ensure the perceived intensity and/or scent of the active composition in the surrounding space remains at a constant, or unchanged for up to one month.

In some aspects, the liquid composition comprises less than 30% by weight ingredients with a vapor pressure greater than 0.2 mmHg at 20° C., and less than 40% by weight ingredients with a vapor pressure of less than 0.01 mmHg at 20° C. Alternatively, the liquid composition comprises less than 20% by weight ingredients with a vapor pressure greater than 0.2 mmHg at 20° C., and less than 30% by weight ingredients with a vapor pressure of less than 0.01 mmHg at 20° C. Alternatively, the liquid composition comprises less than 15% by weight ingredients with a vapor pressure greater than 0.2 mmHg at 20° C., and less than 25% by weight ingredients with a vapor pressure of less than 0.01 mmHg at 20° C.

Although special mention has been made hereinabove of the perfuming effect that can be exerted by the devices of the present disclosure, the same principles apply to analogous devices for the diffusion of deodorizing or sanitizing vapors, the perfume being replaced by a deodorizing composition, an antibacterial, an insecticide, an insect repellent or an insect attractant. As used herein, the term "sanitizing vapors", refers to the vapors of those substances which can enhance the degree of acceptance of the air surrounding the observer, but also to those substances which can exert an attractant or repellent effect towards certain species of insects, for instance towards houseflies or mosquitoes, or else, which can have bactericide or bacteriostatic activity. In some aspects, mixtures of such agents can also be used.

Accordingly, in some aspects, the porous material is configured to ensure that the amount of active composition that evaporates from the body portion (1) is in an amount sufficient to ensure the active composition is at, or above an amount necessary to achieve its desired effect in the surrounding space.

In some aspects, the total surface area of the plurality of honeycomb structures is configured to ensure the amount of active composition that is absorbed by the body portion (1) is in an amount sufficient to ensure the amount of active composition that is released from the device into the surrounding space remains relatively constant throughout the lifetime of the device, and/or is in an amount sufficient to be above an amount necessary to achieve its desired effect in the surrounding space.

In some aspects, the plurality of honeycomb structures (2) increase the total surface area:volume ratio of the device, such that the surface area:volume ratio of the device is configured to ensure the amount of active composition that is absorbed by the body portion (1) is in an amount sufficient to ensure the amount of active composition that is released from the device into the surrounding space remains relatively constant throughout the lifetime of the device, and/or is in an amount sufficient to be above an amount necessary to achieve its desired effect in the surrounding space.

In some aspects, the active composition comprises ingredients having vapor pressures sufficient to ensure the amount of active composition that is released from the device into the surrounding space remains relatively constant throughout the lifetime of the device, and/or is in an amount sufficient to be above an amount necessary to achieve its desired effect in the surrounding space.

In some aspects, the active composition may also contain optional ingredients acting as, for example, solvents, thickeners, anti-oxidants, dyes, bittering agents and UV inhibitors.

In some aspects, the active composition further comprises one or more solvents. In some aspects, the one or more solvents may be useful to have a single-phase liquid and/or to modulate the speed of evaporation of the active composition into the surrounding air. The solvents may belong to the families of isoparaffins, paraffins, hydrocarbons, glycols, glycol ethers, glycol ether esters, esters or ketones.

Examples of commercially available solvents suitable for use in the present disclosure include the solvents known under the tradename Isopar® H, J, K, L, M, P or V (isoparaffins; origin: Exxon Chemical), Norpar® 12 or 15 (paraffins; origin: Exxon Chemical), Exxsol® D 155/170, D 40, D 180/200, D 220/230, D 60, D 70, D 80, D 100, D 110 or D 120 (dearomatised Hydrocarbons; origin: Exxon Chemical), Dowanol® PM, DPM, TPM, PnB, DPnB, TPnB, PnP or DPnP (glycol ethers; origin: Dow Chemical Company), Eastman® EP, EB, EEH, DM, DE, DP or DB (glycol ethers; origin: Eastman Chemical Company), Dowanol® PMA or PGDA (glycol ether esters; origin: Dow Chemical Company) or Eastman® EB acetate, Eastman® DE acetate, Eastman® DB acetate, Eastmanm EEP (all glycol ether esters; all origin: Eastman Chemical Company).

Other solvents suitable for use in the present disclosure include dipropylene glycol, propylene glycol, ethylene glycol ethyl ether acetate, ethylene glycol diacetate, isopropyl myristate, diethyl phthalate, 2-ethylhexyl acetate, methyl n-amyl ketone or di-isobutyl ketone.

In some aspects, the total amount of solvents present in the active composition may vary between 0.0% and 80%, alternatively between 30% and 70%, the percentages being relative to the weight of the active composition.

Non-limiting examples of useful thickener ingredients include ethyl cellulose (commercial examples of which are available from Hercules Inc.), fumed silica (commercial examples of which are available from Degussa) and styrene-butadiene-styrene block copolymers (commercial examples of which are available from Shell).

In some aspects, the total amount of thickeners present in the active composition may vary between 0.0% and 10%, alternatively between 1% and 4%, the percentages being relative to the weight of the active composition.

Non-limiting examples of useful antioxidant ingredients include sterically hindered amines, i.e. the derivatives of the 2,2,6,6-tetramethyl-piperidine, such as those known under the tradename Uvinul® (origin BASF AG) or Tinuvin® (origin: Ciba Speciality Chemicals), as well as the alkylated hydroxyarene derivatives, such as butylated hydroxytoluene (BHT).

In some aspects, the total amount of antioxidants present in the active composition may vary between 0.0% and 10%, alternatively between 1% and 4%, the percentages being relative to the weight of the active composition.

Other optional ingredients of the active composition comprise dyes. Suitable dyes may be oil-soluble and can be found in the Colour Index International, published by The Society of Dyers and Colourist. Non-limiting examples of suitable dyes include derivatives of the anthraquinone, methine, azo, triarylmethane, triphenylmethane, azine, aminoketone, spirooxazine, thioxanthene, phthalocyanine, perylene, benzopyran or perinone families Examples of such dyes which are commercially available are known under the tradename Sandoplast® Violet RSB, Violet FBL, Green GSB, Blue 2B or Savinyl® Blue RS (all anthraquinone derivatives; origin: Clariant Huningue S.A.), Oilsol® Blue DB (anthraquinone; origin: Morton International Ltd.), Sandoplast® Yellow 3G (methine; origin: Clariant Huningue S.A.), Savinyl® Scarlet RLS (azo metal complex; origin: Clariant Huningue S.A.), Oilsol® Yellow SEG (monoazo; origin: Morton International Ltd.), Fat Orange® R (monoazo; origin: Hoechst AG), Fat Red® SB (diazo; origin: Hoechst AG), Neozapon® Blue 807 (phtalocyanine; origin: BASF AG), Fluorol® Green Golden (perylene; origin: BASF AG).

In some aspects, the total amount of dyes present in the active composition may vary between 0.0% and 0.5%, alternatively between 0.005% and 0.05%, the percentages being relative to the weight of the active composition.

In some aspects, a bittering agent may be desirable in order to render the product unpalatable, making less likely that the active composition is ingested, especially by young children. Non-limiting examples of bittering agents include isopropyl alcohol, methyl ethyl ketone, methyl n-butyl ketone or yet a denatonium salt such as the denatonium benzoate known also under the trademark Bitrex™ (origin: Mac Farlan Smith Ltd.).

The bittering agent may be incorporated in the active composition in a total amount comprised between 0.0% and 5%, the percentages being relative to the total weight of the active composition. In the case of Bitrex™ the amount can be comprised between 0.0% and 0.1%, alternatively between 0.001% to 0.05% of the total weight of the active composition.

Non-limiting examples of useful UV-inhibitor ingredients, include benzophenones, diphenylacrylates or cinnamates such as those available under the trade name Uvinul® (origin: BASF AG).

In some aspects, the total amount of UV-inhibitors present in the active composition may vary between 0.0% and 0.5%, alternatively between 0.01% and 0.4%, the percentages being relative to the total weight of the active composition.

In some aspects, the active composition comprises ingredients having a vapor pressure between 4 Pa and 270 Pa, the vapor pressure being measured at 20° C. In some aspects, the vapor pressure is sufficient to ensure that a relatively constant composition is maintained over the lifetime of the device and that the active composition evaporates at a relatively steady rate during the life of the product. In some aspects, at least 60% by weight of the active composition comprises ingredients having a vapor pressure between 4 Pa and 270 Pa, the vapor pressure being measured at 20° C.

In some aspects, at least 80% by weight of the active composition comprises ingredients having a vapor pressure comprised between 4 Pa and 270 Pa.

Methods Utilizing a Device According to Some Aspects Presented Herein:

Some aspects provide a method of dispensing an active composition into a surrounding space, comprising providing a device according to some aspects presented herein, placing the device into a space, and allowing the active composition to evaporate from the device.

Kits:

Some aspects provide a kit, comprising a device according to some aspects presented herein and at least one active composition, wherein a user may select a particular active composition from the at least one active composition, and utilize the selected at least one active composition according to the aspects presented herein.

The present disclosure is best illustrated but is not limited to the following examples.

EXAMPLES

Example 1

An air freshener dispenser in accordance with the present disclosure was constructed as illustrated in FIG. 1. The device was a cube, where each side of the cube is 46 mm, and a bulk volume of approximately 100 cm$^3$. The density of the plurality of cells was 100 cells per square inch, the thickness of the wall (3) of the individual cells was 0.50 mm, and the spacing (p) of each individual cell was 2.54 mm. Accordingly, the body portion (1) comprised 324 cells, in an 18×18 array. The surface area of each cell was 375 mm$^2$. Accordingly, the total surface area of the plurality of cells was 121500 mm$^2$ (1215 cm$^2$ or 188 sq·in. or 1.3 sq·ft).

Example 2

An air freshener dispenser in accordance with the present disclosure was constructed, wherein the device was cuboidal, having a width and length of 43 mm, and a height of 42 mm. The cells were hexagonal, the density of the plurality of cells was 200 cells per square inch. The thickness of the wall (3) of the individual cells was 0.37 mm. The cells were arranged in an array of 585 cells. The surface area of each cell was 213 mm$^2$. Accordingly, the total surface area of the plurality of cells was 124989 mm$^2$ (1250 cm$^2$ or 194 sq·in. or 1.34 sq·ft).

Example 3

An air freshener dispenser in accordance with the present disclosure was constructed as illustrated in FIG. 1. The device was cube, where each side of the cube was 46 mm, and a bulk volume of approximately 100 cm$^3$. The density of the plurality of cells was 300 cells per square inch, the thickness of the wall (3) of the individual cells was 0.30 mm, and the spacing (p) of each individual cell was 1.47 mm. Accordingly, the body portion (1) comprised 961 cells, in a 31×31 array. The surface area of each cell was 215 mm$^2$. Accordingly, the total surface area of the plurality of cells was 206616 mm$^2$ (2066 cm$^2$ or 320 sq·in. or 2.2 sq·ft).

Example 4

An air freshener dispenser in accordance with the present disclosure is constructed as illustrated in FIG. 1. The body portion (1) is formed from activated charcoal. The body portion is filled with a perfuming composition, and the total mass of device is recorded. The device is then placed in a temperature-humidity controlled test room (at 20° to 22° C. and 45% to 55% relative humidity) and the weights recorded at regular intervals up to 45 days.

The purpose of this Example is to demonstrate that the device is capable of dispersing the active composition, as evidenced by a decrease in weight of the device over time. Additionally, the purpose of this Example is to demonstrate that the device is capable of dispersing the active composition at a uniform rate.

Example 5

An air freshener dispenser in accordance with the present disclosure is constructed as illustrated in FIG. 1. The body portion (1) is formed from activated charcoal. The body portion is filled with a perfuming composition, and the total mass of device is recorded. The device is then placed in a temperature-humidity controlled test room (at 20° to 22° C. and 45% to 55% relative humidity) and the weights recorded at regular intervals up to 45 days. In parallel, a second, identical device is constructed. The second device is then placed in a temperature-humidity controlled test room (at 20° to 22° C. and 45% to 55% relative humidity), a continuous flow of air is introduced through the body portion and the weights recorded at regular intervals up to 45 days.

The purpose of this Example is to demonstrate that the device is capable of dispersing the active composition, as evidenced by a decrease in weight of the device over time. Additionally, the purpose of this Example is to demonstrate that rate of dispersion is increased by the introduction of airflow through the body portion.

Example 6

An air freshener dispenser in accordance with the present disclosure is constructed as illustrated in FIG. 1. The body portion (1) is formed from activated charcoal. The body portion is filled with a perfuming composition, and the total mass of device is recorded. The device is then placed in a temperature-humidity controlled test room (at 20° to 22° C. and 45% to 55% relative humidity) and the weights recorded at regular intervals up to 45 days. In addition, samples of the headspace are obtained and the concentration of perfume composition is determined. In parallel, a second, identical device is constructed. The second device is then placed in a temperature-humidity controlled test room (at 20° to 22° C. and 45% to 55% relative humidity), a continuous flow of air is introduced through the body portion and the weights recorded at regular intervals up to 45 days. In addition, samples of the headspace are obtained and the concentration of perfume composition is determined.

The purpose of this Example is to demonstrate that the device is capable of dispersing the active composition, as evidenced by a decrease in weight of the device over time. Additionally, the purpose of this Example is to demonstrate that rate of dispersion is increased by the introduction of airflow through the body portion.

Finally, the purpose of this Example is to demonstrate that the device is capable of dispensing the active composition above the odor threshold of the active composition.

Example 7

An air freshener dispenser in accordance with the present disclosure is constructed as illustrated in FIG. 1. The body portion (1) is formed from activated charcoal. The body portion is filled with a perfuming composition, and the total mass of device is recorded. The device is then placed in a temperature-humidity controlled test room (at 20° to 22° C. and 45% to 55% relative humidity) and the weights recorded at regular intervals up to 45 days. In parallel, identical devices are constructed. The identical devices are placed in a temperature-humidity controlled test room (at 20° to 22° C. and 45% to 55% relative humidity), a flow of air is introduced through the body portion, wherein the rate of airflow for each device is different, and the weights recorded at regular intervals up to 45 days.

The purpose of this Example is to demonstrate that the device is capable of dispersing the active composition, as evidenced by a decrease in weight of the device over time. Additionally, the purpose of this Example is to demonstrate that rate of dispersion is increased by the introduction of airflow through the body portion, and the rate of dispersion is proportional to the rate of airflow through the body portion (1).

Example 8

An air freshener dispenser in accordance with the present disclosure is constructed as illustrated in FIG. 1. The body portion (1) is formed from activated charcoal. The body portion is filled with a perfuming composition, and the total mass of device is recorded. The device is then placed in a temperature-humidity controlled test room containing a test malodor (at 20° to 22° C. and 45% to 55% relative humidity)

and the weights recorded at regular intervals up to 45 days. In parallel, identical devices are constructed. The identical devices are placed in a temperature-humidity controlled test room containing a test malodor (at 20° to 22° C. and 45% to 55% relative humidity), a flow of air is introduced through the body portion, wherein the rate of airflow for each device is different, and the weights recorded at regular intervals up to 45 days. In addition, samples of the headspace are obtained and the concentration of the perfume composition and the test malodor is determined.

The purpose of this Example is to demonstrate that the device is capable of dispersing the active composition, as evidenced by a decrease in weight of the device over time. Additionally, the purpose of this Example is to demonstrate that rate of dispersion is increased by the introduction of airflow through the body portion.

Additionally, the purpose of this Example is to demonstrate that the device is capable of removing the test malodor from the test room.

Finally, the purpose of this Example is to demonstrate that the device is capable of dispensing the active composition above the odor threshold of the active composition.

Example 9

An air freshener dispenser as described in Example 2 was fabricated from activated charcoal and clay minerals. The mass of the dispenser prior to loading with the test active composition was 27.96 g. The dispenser was immersed for 5 minutes in FlexiSolv® DBE®-LVP esters (a mixture comprising dimethyl adipate and dimethyl glutarate; origin: Invista). The dispenser was then removed from the liquid and the excess liquid allowed to drain from its surface. The mass of the dispenser after immersion was 37.11 g; therefore, the mass of active composition absorbed into the body of the dispenser was 9.15 g.

The device was then placed in a temperature and humidity controlled test room (at 20° to 22° C. and 45% to 55% relative humidity) and the mass recorded at regular intervals up to 30 days. The cumulative mass of active composition evaporated from the device at each interval is shown in Table 1 below.

TABLE 1

Evaporation of FlexiSolv ® DBE ®-LVP esters from a device according to an aspect presented herein

| Elapsed Time (t) (days) | Recorded Mass (m) (g) | Cumulative Weight Loss (cwl) (g) |
|---|---|---|
| 0 | 37.11 | 0.00 |
| 3 | 35.28 | 1.83 |
| 7 | 33.63 | 3.48 |
| 14 | 31.51 | 5.60 |
| 21 | 30.81 | 6.30 |
| 28 | 30.32 | 6.79 |

In parallel, a second, identical device was prepared in an identical manner to the first. The mass of the dispenser prior to loading with the test active composition was 29.00 g. The mass of the dispenser after immersion was 38.29 g; therefore, the mass of volatile material absorbed into the body of the dispenser was 9.27 g.

The second device was then placed in a temperature and humidity controlled test room (20° to 22° C. and 45% to 55% relative humidity). Air was blown continuously through the cells of the body portion of the dispenser at a velocity of approximately 1 m/s by means of an axial fan (AC Infinity model #8025). The mass of the second device was recorded at regular intervals up to 8 hours, with a final recording being made after 1 day had elapsed. The cumulative mass of active composition evaporated from the device at each interval is shown in Table 2 below.

TABLE 2

Evaporation of FlexiSolv ® DBE ®-LVP esters from a device according to an aspect presented herein

| Elapsed Time (t) (hours) | Recorded Mass (m) (g) | Cumulative Weight Loss (cwl) (g) |
|---|---|---|
| 0.00 | 38.27 | 0.00 |
| 0.33 | 38.08 | 0.19 |
| 1.33 | 37.61 | 0.66 |
| 2.33 | 37.06 | 1.21 |
| 4.83 | 35.71 | 2.56 |
| 7.83 | 34.45 | 3.82 |
| 24.33 | 30.43 | 7.84 |

The purpose of this Example is to demonstrate that the device of the present disclosure is capable of dispersing an active composition, as evidenced by a decrease in weight of the device over time.

Additionally, the purpose of this Example is to demonstrate that rate of dispersion is increased by the introduction of airflow through the body portion. In this Example, the airflow increases that rate of evaporation by a factor of approximately 26. That is, the device with air flowing through the cells of the body portion dispersed approximately the same amount of volatile substance in one minute as the device with no airflow dispersed in approximately 26 minutes.

Example 10

Five air freshener dispensers as described in Example 2 were fabricated from activated charcoal and clay minerals. The mass of each dispenser prior to loading with the test active composition was recorded and then each dispenser was immersed for 5 minutes in FlexiSolv® DBE®-LVP esters (a mixture comprising dimethyl adipate and dimethyl glutarate; origin: Invista). The five dispensers were removed from the liquid and the excess liquid allowed to drain from their surfaces. The mass of each dispenser after immersion was recorded and the mass of volatile material absorbed into the body each dispenser calculated.

The five devices were then placed in a temperature and humidity controlled test room (20° to 22° C. and 45% to 55% relative humidity). Air was blown through the cells of the body portion of each dispenser at a velocity of approximately 1 m/s by means of axial fans (AC Infinity model #8025), one axial fan for each dispenser. Each fan unit was connected to a programmable plug-in electrical switch that allowed the frequency at which air was blown through each dispenser to be controlled. Each of the switches was programmed with different on/off cycle times, as described in Table 3. The mass of each dispenser was recorded at regular intervals up to 21 days. The cumulative mass of active composition evaporated from each device is shown in Table 3 below.

TABLE 3

Evaporation of FlexiSolv ® DBE ®-LVP esters from a devices according to an aspect presented herein

| Elapsed Time (t) (days) | Cumulative Weight Loss (cwl) (g) | Cumulative Weight Loss (cwl) (g) | Cumulative Weight Loss (cwl) (g) | Cumulative Weight Loss (cwl) (g) | Cumulative Weight Loss (cwl) (g) |
|---|---|---|---|---|---|
| 0 | 0.00 | 0.00 | 0.00 | 0.00 | 0.00 |
| 1 | 5.39 | 3.87 | 3.30 | 2.11 | 1.60 |
| 3 | 7.92 | 6.50 | 6.06 | 4.59 | 3.57 |
| 7 | 9.03 | 8.25 | 7.82 | 6.55 | 5.68 |
| 10 | — | 8.85 | 8.56 | 7.43 | 6.63 |
| 14 | — | 9.18 | 8.94 | 8.32 | 7.61 |
| 17 | — | — | 9.03 | 8.74 | 8.19 |
| 21 | — | — | — | 8.96 | 8.65 |
| Initial amount of FlexiSolv ® absorbed | 9.20 g | 9.31 g | 9.22 g | 9.14 g | 9.25 g |
| Fan "on" time | 10 minutes | 10 minutes | 5 minutes | 2 minutes | 2 minutes |
| Fan "off" time | 10 minutes | 20 minutes | 15 minutes | 13 minutes | 18 minutes |

The purpose of this Example is to demonstrate that the rate of evaporation of the active substance from a device according to an aspect presented herein can be controlled by adjusting the frequency at which air is blown through the body of the device.

Example 11

Five air freshener dispensers as described in Example 2 were fabricated from activated charcoal and clay minerals. The mass of each dispenser prior to loading with the test active composition comprising perfume raw materials was recorded and then each dispenser was immersed for 5 minutes in a different perfume raw material. The five dispensers were removed from the perfume raw materials and the excess liquid allowed to drain from their surfaces. The mass of each dispenser after immersion was recorded and the mass of perfume raw material absorbed into the body each dispenser was calculated. The perfume raw materials used in this Example and the respective amounts absorbed in each of the devices are shown in Table 4 below.

TABLE 4

Perfume raw materials absorbed into devices according to an aspect described herein

| Perfume Raw Material | Mass of Device Prior to Loading (g) | Mass of Device After Loading (g) | Mass of Perfume Material Absorbed (g) |
|---|---|---|---|
| Isononyl acetate | 29.02 | 34.92 | 5.90 |
| Floropal | 29.15 | 36.76 | 7.61 |
| Linalyl acetate | 29.15 | 35.62 | 6.47 |
| Phenylacetaldehyde | 29.15 | 37.01 | 7.86 |
| Verdyl acetate | 29.15 | 37.35 | 8.20 |

The five devices were then placed in a temperature and humidity controlled test room (20° to 22° C. and 45% to 55% relative humidity) and the mass of each device recorded at intervals up to 38 days. The cumulative mass of active composition evaporated from each of the devices is shown in Table 5 below.

TABLE 5

Cumulative weight loss (cwl) of perfume raw materials from devices according to an aspect presented herein

| Elapsed Time (days) | Isononyl Acetate | Floropal | Linalyl Acetate | Phenylacet-aldehyde | Verdyl Acetate |
|---|---|---|---|---|---|
| 0 | 0.00 | 0.00 | 0.00 | 0.00 | 0.00 |
| 1 | 1.89 | −0.12 | 0.53 | 0.07 | −0.14 |
| 10 | 6.28 | 2.07 | 5.92 | 1.15 | 2.00 |
| 15 | 6.25 | 3.12 | 6.54 | 1.38 | 3.11 |
| 38 | 6.17 | 6.14 | 6.60 | 1.78 | 6.49 |

The purpose of this Example is to demonstrate that devices according to the aspects presented herein are capable of dispersing a variety of active compositons, as evidenced by a weight loss of materials from the device over time. It is evident that isononyl acetate and linalyl acetate evaporated quickly from the device whereas phenylacetaldehyde evaporated slowly. Floropal and verdyl acetate evaporated at a consistent rate during the 38 day test period.

Example 12

An air freshener dispenser in accordance with the present disclosure was constructed from the ceramic cordierite comprising from about 32% to about 38% $Al_2O_3$, and from about 48% to about 54% $SiO_2$ and from about 12% to about 16% MgO. The device was a cylinder comprising a diameter of 20 mm and a height of 20 mm. The density of the plurality of cells was 400 cells per square inch, the thickness of the wall (3) of the individual cells was 0.15 mm, and the spacing (p) of each individual cell was 1.10 mm. Accordingly, the body portion (1) comprised a total surface area of the plurality of cells of approximately 14,800 $mm^2$ (148 $cm^2$).

Example 13

An air freshener dispenser in accordance with the present disclosure was constructed from the ceramic cordierite comprising from about 32% to about 38% $Al_2O_3$, and from about 48% to about 54% $SiO_2$ and from about 12% to about 16% MgO. The device was a cylinder comprising a diameter of 33 mm and a height of 5.5 mm. The density of the plurality of cells was 400 cells per square inch, the thickness of the wall (3) of the individual cells was 0.15 mm, and the spacing (p) of each individual cell was 1.10 mm. Accordingly, the body portion (1) comprised a total surface area of the plurality of cells of approximately 11,100 mm² (111 cm²).

Example 14

An air freshener dispenser in accordance with the present disclosure was constructed from the ceramic cordierite comprising from about 32% to about 38% $Al_2O_3$, and from about 48% to about 54% $SiO_2$ and from about 12% to about 16% MgO. The device was a cylinder comprising a diameter of 25 mm and a height of 100 mm. The density of the plurality of cells was 400 cells per square inch, the thickness of the wall (3) of the individual cells was 0.15 mm, and the spacing (p) of each individual cell was 1.10 mm. Accordingly, the body portion (1) comprised a total surface area of the plurality of cells of approximately 115,600 mm² (1,156 cm²).

Example 15

An air freshener dispenser in accordance with the present disclosure was constructed from the ceramic cordierite comprising from about 32% to about 38% $Al_2O_3$, and from about 48% to about 54% $SiO_2$ and from about 12% to about 16% MgO. The device was a cylinder comprising a diameter of 25 mm and a height of 50 mm. The density of the plurality of cells was 400 cells per square inch, the thickness of the wall (3) of the individual cells was 0.15 mm, and the spacing (p) of each individual cell was 1.10 mm. Accordingly, the body portion (1) comprised a total surface area of the plurality of cells of approximately 57,800 mm² (578 cm²).

Example 16

An air freshener dispenser as described in Example 2 was fabricated from activated charcoal and clay minerals. The mass of the dispenser prior to loading with the active composition was 28.65 g. The dispenser was immersed for 5 minutes in an active composition comprising fragrance composition (Black Berry and Bay MSR 296385 M2; origin: Firmenich). The dispenser was then removed from the liquid and the excess liquid allowed to drain from its surface. The mass of the dispenser after immersion was 37.62 g; therefore, the mass of the active composition absorbed into the body of the dispenser was 8.97 g.

The device was then placed in a temperature and humidity controlled test room (at 20° to 22° C. and 45% to 55% relative humidity) and the mass recorded at regular intervals up to 28 days. The cumulative mass of volatile substance evaporated from the device at each interval is shown in Table 6 below.

TABLE 6

Evaporation of fragrance composition from a device of the invention

| Elapsed Time (t) (days) | Recorded Mass (m) (g) | Cumulative Weight Loss (cwl) (g) |
| --- | --- | --- |
| 0 | 37.62 | 0.00 |
| 1 | 37.25 | 0.37 |
| 4 | 35.95 | 1.67 |
| 8 | 34.54 | 3.08 |
| 10 | 34.18 | 3.44 |
| 14 | 33.72 | 3.90 |

TABLE 6-continued

Evaporation of fragrance composition from a device of the invention

| Elapsed Time (t) (days) | Recorded Mass (m) (g) | Cumulative Weight Loss (cwl) (g) |
| --- | --- | --- |
| 22 | 33.28 | 4.34 |
| 28 | 32.97 | 4.65 |

Additionally, at intervals during the 28 day test period, the intensity of fragrance released from the device was assessed. A 300 ft³ evaluation cabin was used for the sensory evaluation of the sample. The environmental conditions in the cabin during the test were 72° F., 35% RH with 5 air changes per hour. A portable desk fan, set on low, was placed at the floor of the cabin to circulate the air within. The sample was placed in the cabin and allowed to equilibrate for one hour prior to evaluation. The cabin was assessed by between 20 and 24 untrained but experienced assessors. By "untrained but experienced assessors" we mean individuals who have not received formal olfactive training but who are used to participating in fragrances assessments and have experience in rating the odor attributes.

All assessors were instructed to smell the odor in the cabin, and rate the intensity of the odor using a 1 to 7 category scale, where 1 indicates no perceivable odor and 7 indicates very strong odor. The average intensity rating of fragrance from the device during the testing period is shown in Table 7 below.

TABLE 7

Perceived intensity of fragrance composition released from a device of the invention

| Elapsed Time (days) | Average Perceived Intensity |
| --- | --- |
| 0 | 4.56 |
| 7 | 4.61 |
| 14 | 3.94 |
| 21 | 3.70 |
| 28 | 3.48 |

The purpose of this Example is to demonstrate that devices of the present disclosure are capable of dispersing a fragrance composition, as evidenced by a weight loss of the active composition from the device over time. A second purpose of this Example is to demonstrate that the device is capable of dispensing the fragrance composition into a room at a level that it can be readily perceived by human subjects.

Publications cited throughout this document are hereby incorporated by reference in their entirety. Although the various aspects of the disclosure have been illustrated above by reference to examples and preferred embodiments, it will be appreciated that the scope of the disclosure is defined not by the foregoing description but by the following claims properly construed under principles of patent law.

The invention claimed is:

1. A device comprising:
   a) a body portion,
      wherein the body portion comprises a honeycomb comprised of a porous material,
      wherein the honeycomb comprises a plurality of individual cells bounded with one another,
      wherein the plurality of individual cells are bounded at a density, wherein each cell within the plurality comprises a hollow tube, having a wall, a first end, and a second end, wherein the wall has an inner surface defining an inner dimension of the hollow tube, wherein the wall has a thickness, wherein the first and second ends of the tube are open, wherein the first end of each individual cell within the plurality are aligned, wherein the second end of each individual cell within the plurality are aligned, wherein the distance between the first end and the second end of each individual cell within the plurality, and the inner dimension of the hollow tube of each individual cell within the plurality define a volume of each individual cell within the plurality, wherein the distance between the first end and the second end of each individual cell within the plurality, the inner surface and inner dimension of the hollow tube of each individual cell within the plurality define a surface area within each individual cell within the plurality, wherein the sum of each surface area within each individual cell within the plurality defines a total surface area of the plurality of cells, wherein a first end of the plurality of cells define a bottom surface of the body portion, wherein a second end of the plurality of cells define a top surface of the body portion, wherein the body portion has at least one side surface, wherein the at least one side surface is continuous planar surface; and b) an active composition, wherein each individual cell within the plurality is configured to draw in the active composition into the volume, wherein the porous material of the body portion is configured to absorb the active composition, and wherein the porous material of the body portion is configured to disperse the active composition via evaporation;

wherein the porous material is a mixture of charcoal and clay;

wherein the device is cuboidal, having a width and length of 43 mm, and a height of 42 mm.

2. The device of claim 1, wherein the individual cells within the plurality have a cross-sectional shape selected from the group consisting of: an irregular shape, a square, a rectangle, a circle, an ellipse, a rhombus, a semi-circle, and a trapezium.

3. The device of claim 1, wherein the individual cells within the plurality are co-aligned.

4. The device of claim 1, wherein the individual cells within the plurality are straight.

5. The device of claim 1, wherein the density is from 50 to 1000 cells per square inch.

6. The device of claim 1, wherein the porous material of the body portion is configured to disperse the active composition via evaporation for a period of time up to one month.

7. The device of claim 1, wherein the device further comprises a reservoir, configured to fluidly connect with the bottom surface of the device, wherein fluid connection is configured to draw the active composition into the volume of each individual cell within the plurality.

8. The device of claim 1, wherein the dispensing of the active composition via evaporation is increased by increasing airflow through the plurality of cells from the first end and the second end of the plurality of cells.

9. The device of claim 1, wherein the porous material of the body portion is configured to absorb molecules having malodors.

10. The device of claim 9, wherein the absorption of molecules having malodors is increased by increasing airflow through the plurality of cells from the first end and the second end of the plurality of cells.

11. A method of dispensing an active composition into a surrounding space, comprising placing the device of claim 1 into a space in need thereof, and allowing the active composition to evaporate from the device.

12. A kit, comprising the device according to claim 1 and at least one active composition.

13. The device of claim 1, wherein the density is 200 cells per square inch.

14. The device of claim 1, wherein the individual cells within the plurality have a hexagonal cross-sectional shape.

15. The device of claim 1, wherein the thickness of the wall of each individual cell is 0.37 mm.

16. The device of claim 1, wherein the cells are arranged in an array of 585 cells.

17. The device of claim 1, wherein the surface area of each cell is 213 $mm^2$.

18. The device of claim 1, wherein the total surface area of the plurality of cells is 124989 $mm^2$.

* * * * *